(12) United States Patent
Tevlin

(10) Patent No.: US 11,230,729 B2
(45) Date of Patent: Jan. 25, 2022

(54) METHODS AND DEVICES FOR OBTAINING CELLULAR AND DNA MATERIAL FROM HUMAN FEMALE REPRODUCTIVE SYSTEM

(71) Applicant: Inanna Diagnostics, Inc., Newton, MA (US)

(72) Inventor: Maya Tevlin, Bayside, NY (US)

(73) Assignee: INANNA DIAGNOSTICS, INC, Bayside, NY (US)

( * ) Notice: Subject to any disclaimer, the term of this patent is extended or adjusted under 35 U.S.C. 154(b) by 0 days.

(21) Appl. No.: 16/278,151

(22) Filed: Feb. 17, 2019

(65) Prior Publication Data

US 2019/0323058 A1   Oct. 24, 2019

Related U.S. Application Data

(60) Provisional application No. 62/660,861, filed on Apr. 20, 2018, provisional application No. 62/660,850, filed on Apr. 20, 2018, provisional application No. 62/660,858, filed on Apr. 20, 2018, provisional application No. 62/660,866, filed on Apr. 20, 2018.

(51) Int. Cl.
| | | |
|---|---|---|
| *C12Q 1/24* | (2006.01) | |
| *C12N 5/071* | (2010.01) | |
| *C12N 5/10* | (2006.01) | |
| *C12N 15/10* | (2006.01) | |

(52) U.S. Cl.
CPC ............. *C12Q 1/24* (2013.01); *C12N 5/0682* (2013.01); *C12N 15/1003* (2013.01)

(58) Field of Classification Search
CPC ..................................................... C12Q 1/24
See application file for complete search history.

(56) References Cited

U.S. PATENT DOCUMENTS

| | | | | |
|---|---|---|---|---|
| 6,342,387 | B1* | 1/2002 | Hayashizaki | C12N 15/1006 435/270 |
| 8,152,739 | B1* | 4/2012 | McCully | A61B 10/0291 600/569 |
| 2005/0123914 | A1 | 6/2005 | Katz et al. | |
| 2008/0262384 | A1* | 10/2008 | Wiederkehr | G01N 33/57411 600/569 |
| 2011/0027795 | A1 | 2/2011 | Mantzaris et al. | |
| 2015/0267240 | A1 | 9/2015 | Armant et al. | |

(Continued)

FOREIGN PATENT DOCUMENTS

| | | | |
|---|---|---|---|
| WO | 03/020986 A1 | 3/2003 | |
| WO | WO-03020986 A1 * | 3/2003 | ........... C12Q 1/6881 |
| WO | 2005/084103 A2 | 9/2005 | |

OTHER PUBLICATIONS

Brule ( Journal of Clinical Microbiology (1990) vol. 28, pp. 2739-2743).*

(Continued)

*Primary Examiner* — Jeanine A Goldberg
*Assistant Examiner* — Jennifer L. Overly
(74) *Attorney, Agent, or Firm* — Troutman Pepper Hamilton Sanders LLP

(57) ABSTRACT

Efficient harvesting of cells, cell fragments, free nuclei, and DNA material from female reproductive system is made possible by processing gelatinous part of cervical mucus. Rinsing may be used to separate the gelatinous part of cervical mucus from the remainder of the cervical mucus sample.

6 Claims, 8 Drawing Sheets

(56) References Cited

U.S. PATENT DOCUMENTS

| | | |
|---|---|---|
| 2015/0292027 A1 | 10/2015 | Kinde et al. |
| 2016/0076980 A1 | 3/2016 | Shuber et al. |
| 2017/0051347 A1 | 2/2017 | Vogelstein et al. |

OTHER PUBLICATIONS

Fukuda (gynecologic oncology (1999) vol. 72, pp. 273-277).*
Miller (American Family Physician (1999) vol. 59, pp. 440-443).*
Patel (BJOG (2010) vol. 117, pp. 1051-1059).*
Kim (Analytical and Quantitative Cytopathology and histopathology (2012) vol. 34, pp. 195-203.*
Pappa (gynceological oncology (2006) vol. 100, pp. 596-600).*
Blalock, Emily Comparative Study of HPV 16 and HP)V 18 Antibody Detection in Serum, Cervical Mucus and Oral Mucosal Transudate, Biology Thesis, Georgia State University 2008. (Year: 2008).*
Othman et al. Adequacy of cellular material in split-sampling of cervical scrapings for routine cancer screening: an analysis of 702 smears (2012) Malaysian J Pathol 34(2): 115-121 (Year: 2012).*
Kinde et al. Evaluation of DNA from the Papanicolaou Test to Detect Ovarian and Endometrial Cancers (2013) Science Translational Medicine 5:167 12 pages (Year: 2013).*
Bolnick et al., Altered Biomarkers in TrophoblastCells Obtained Noninvasively Prior to Clinical Manifestation of Perinatal Disease, Sci. Rep. 6, 32382; doi: 10.1038/srep32382 (2016).
Asadpour et al., Ovine fetal sex determination using circulating cell-free fetal DNA (ccffDNA) and cervical mucous secretions, Asian Pacific Journal of Reproduction 2015; 4(1): 65-69.
Nott et al., The structure and function of the cervix during pregnancy, Translational Research in Anatomy 2 (2016) 1-7.
Jain et al., Fetal genome profiling at 5 weeks of gestation after noninvasive isolation of trophoblast cells from the endocervical canal, Sci. Transl. Med. 8, 363re4 (2016).
Hatt et al., Characterization of Fetal Cells from the Maternal Circulation by Microarray Gene Expression Analysis—Could the Extravillous Trophoblasts be a Target for Future Cell-Based Non-Invasive Prenatal Diagnosis?, Fetal Diagn Ther., DOI: 10.1159/000356073, 2013.
Katz-Jaffe et al., DNA identification of fetal cells isolated from cervical mucus: potential for early non-invasive prenatal diagnosis, BJOG: an International Journal of Obstetrics and Gynaecology, May 2005, vol. 112, pp. 595-600.
Mantzris et al., Potential of Syncytiotrophoblasts Isolated from the Cervical Mucus for Early Non-lnvasive Prenatal Diagnosis: Evidence of a Vanishing Twin, Clinica Chimica Acta, 438, (2015) 309-315.
Griffith-Jones et al., Detection of fetal DNA in trans-cervical swabs from first trimester pregnancies by gene amplification: a new route to prenatal diagnosis?, British Journal of Obstetrics and Gynaecology, Jun. 1992, vol. 99, pp. 508-51 1.
Miller et al., Transcervical recovery of fetal cells from the lower uterine pole: reliability of recovery and histological/immunocytochemical analysis of recovered cell populations, Human Reproduction vol. 14 No. 2 pp. 521-531, 1999.
Lo et al., Presence of fetal DNA in maternal plasma and serum, Lancet 1997; 350: 485-87.
Cioni et al., Fetal cells in cervical mucus in the first trimester of pregnancy, Prenat Diagn 2003; 23: 168-171.
Imuda et al., Retrieval of trophoblast cells from the cervical canal for prediction of abnormal pregnancy: a pilot study, Human Reproduction, vol. 24, No. 9 pp. 2086-2092, 2009.
Imuda et al., , Transcervical Retrieval of Fetal Cells in the Practice of Modern Medicine: A Review of the Current Literature and Future Direction, Fertil Steril. Apr. 2010 ; 93(6): 1725-1730.
Bolnick et al., Trophoblast retrieval and isolation from the cervix (TRIC) for noninvasive prenatal screening at 5 to 20 weeks of gestation, Fertility and Sterility® vol. 102, No. 1, Jul. 2014, p. 135-142.
Fritz et al., Trophoblast Retrieval and Isolation from the Cervix (TRIC) is Unaffected by Early Gestational Age or Maternal Obesity, Prenat Diagn. Dec. 2015 ; 35(12): 1218-1222.
Authimoolam et al., Biopolymeric Mucin and Synthetic Polymer Analogs—Their Structure, Function and Role in Biomedical Applications, Polymers 2016, 8, 71.
Celli et al., Helicobacter Pylori Moves Through Mucus by Reducing Mucin Viscoelasticity, PNAS, Aug. 25, 2009, vol. 106, No. 34, 14321-14326.
Lai et al., Nanoparticles Reveal That Human Cervicovaginal Mucus is Riddled with Pores Larger Than Viruses, 598-603, PNAS, Jan. 12, 2010, vol. 107, No. 2.
Nakano et al., Insights into the role of cervical mucus and vaginal pH in unexplained infertility, MedicalExpress (Šao Paulo, online). 2015;2(2): M150207.
Odeblad, The Functional Structure of Human Cervical Mucus, Acta Obstet Gynecol Scand. 1968;47:57-79.
Olmsted et al., Diffusion of Macromolecules and Virus-Like Particles in Human Cervical Mucus, Biophysical Journal vol. 81 Oct. 2001 1930-1937.
Rubin, Mucolytics, Expectorants, and Mucokinetic Medications, Respiratory Care, Jul. 2007 vol. 52 No. 7, 859-865.
Suarez et al., Sperm transport in the female reproductive tract, Human Reproduction Update, vol. 12, No. 1 pp. 23-37, 2006.
Kinde et al., Supplementary Materials for Evaluation of DNA from the Papanicolaou Test to Detect Ovarian and Endometrial Cancers, Jan. 9, 2013, Sci. Transl. Med. 5, 167ra4 (2013).
Wang et al., Supplementary Materials for Evaluation of liquid from the Papanicolaou test and other liquid biopsies for the detection of endometrial and ovarian cancers, Mar. 21, 2018, Sci. Transl. Med. 10, eaap8793 (2018).
Kinde et al., Evaluation of DNA from the Papanicolaou Test to Detect Ovarian and Endometrial Cancers, Sci Transl Med. Jan. 9, 2013; 5(167): 167ra4.
Qiu et al., No evidence of clonal somatic genetic alterations in cancer-associated fibroblasts from human breast and ovarian carcinomas, Nat Genet. May 2008 ; 40(5): 650-655.
The Cancer Genome Atlas Research Network, Integrated Genomic Analyses of Ovarian Carcinoma, Nature; 474 (7353): 609-615.
Zorn et al., Choice of Normal Ovarian Control Influences Determination of Differentially Expressed Genes in Ovarian Cancer Expression Profiling Studies, Clinical Cancer Research, vol. 9, 4811-4818, Oct. 15, 2003.
Traut et al., Cancer of the Uterus: The Vaginal Smear in Its Diagnosis, California and Western Medicine, vol. 59, No. 2, 1943, 121-122.
Patel et al., Endometrial carcinoma detected with SurePath liquid-based cervical cytology: comparison with conventional cytology, Cytopathology 2009, 20, 380-387.
Kinde et al., Detection and quantification of rare mutations with massively parallel sequencing, 9530-9535 | PNAS | Jun. 7, 2011 | vol. 108 | No. 23.
Schorge et al., ThinPrep Detection of Cervical and Endometrial Adenocarcinoma—A Retrospective Cohort Study, Cancer (Cancer Cytopathology) Dec. 25, 2002 / vol. 96 / No. 6, 338-343.
ThinPrep® Pap TestQuick Reference Guide, Endocervical Brush/Spatula Protocol, 2004.
Wang et al., Evaluation of Liquid from the Papanicolaou Test and Other Liquid Biopsies for the Detection of Endometrial and Ovarian Cancers, Sci Transl Med. Mar. 21, 2018; 10(433).
Hubers et al., EGFR mutation analysis in sputum of lung cancer patients: A multitechnique study, Lung Cancer 2013; 82; 38-43.
Weiszhar et al., Induced sputum analysis: step by step, Breathe | Jun. 2013 | vol. 9 | No. 4, 301-306.
Thunnissen, Sputum examination for early detection of lung cancer, J Clin Pathol 2003; 56:805-810.
PCT Search Report and Written Opinion of EPO ISA for PCT/US2019/027841—Completed Jun. 6, 2019.
Rahangdale et al., Manual Liquid-Based Cytology: A Clinical Pilot Study of the VitroPrep Cytology Processing Kit, Acta Cytologica 2014;58:373-377.
Wen et al., Evaluation of the reproducibility of amplicon sequencing with Illumina MiSeq platform, Apr. 28, 2017, PLoS ONE 12(4):e0176716.

(56) References Cited

OTHER PUBLICATIONS

Macconaill et al., Unique, dual-indexed sequencing adapters with UMIs effectively eliminate index crosstalk and significantly improve sensitivity of massively parallel sequencing, Jan. 8, 2018, BMC Genomics (2018) 19:30.

Hong et al., Incorporation of unique molecular identifiers in TruSeq adapters improves the accuracy of quantitative sequencing, BioTechniques 63:221-226 (Nov. 2017).

Grainger et al., Use of a Mucolytic Agent (Cytoclair) in the Preparation of Cell Material for the Detection of Malignant Cells in Sputum, Journal of Clinical Pathology, 1978, 31, 585-590.

Rozendaal et al., PCR based high risk HPV testing is superior to neural network based screening for predicting incident CIN III in women with normal cytology and borderline changes, J Clin Pathol 2000; 53:606-611.

Melkert et al., Prevalence of HPV in cytomorphologically normal, cervical smears, as determined by the polymerase chain reaction, is age-dependent, Int. J. Cancer: 53,919-923 (1993).

Pap Test Collection Guidelines for Cytologic Examination, Rev. May 10, 2017.

Centers for Disease Control and Prevention (CDC); "Ovarian Cancer—What Should I Know About Screening?"; Aug. 15, 2019.

Burnett, Tatnai, M.D.; Pap test: Can it detect ovarian cancer?; Mayo Clinic, Aug. 9, 2019.

Centers for Disease Control and Prevention (CDC); "Uterine Cancer—What Should I Know About Screening?"; Aug. 9, 2019.

Cedars Sinai; "Endometrial Cancer"; pp. 1-4, Dec. 11/2020.

\* cited by examiner

METHODS AND DEVICES FOR OBTAINING CELLULAR AND DNA MATERIAL FROM HUMAN FEMALE REPRODUCTIVE SYSTEM

RELATED APPLICATIONS

This application claims the benefit of priority under 35 USC 119(e) to U.S. Provisional Application No. 62/660,850, filed on Apr. 20, 2018, U.S. Provisional Application No. 62/660,858, filed on Apr. 20, 2018, U.S. Provisional Application No. 62/660,861, filed on Apr. 20, 2018, and U.S. Provisional Application No. 62/660,866, filed on Apr. 20, 2018, which are incorporated herein by reference in their entirety.

FIELD OF THE INVENTION

This invention pertains to obtaining cellular and genetic material from female reproductive system for various purposes including, without limitation, cytological analysis, sequencing, and detection of mutations for, without limitation, detecting, screening, and monitoring ovarian, fallopian tubal, or endometrial cancer or similar diseases.

BACKGROUND

Since the introduction of the Papanicolaou ("Pap") test in 1950, the mortality of cervical cancer in screened populations has been reduced by more than 75%. In contrast, deaths from other cancers of the female reproductive system—cancers of ovaries, fallopian tubes, and uterus—have not substantially decreased during that same time period. As a result, more than 60,000 women in the U.S. are diagnosed with ovarian, fallopian tubal, and endometrial (uterus lining) cancer each year. Although endometrial cancer is more common than ovarian cancer, the latter is more lethal. In the U.S., approximately 15,000 and 8,000 women are expected to die each year from ovarian and endometrial cancers, respectively. World-wide, over 200,000 deaths from these tumors are expected this year alone. The mortality associated with undetected gynecologic malignancies has made the development of effective screening tools and methods a high priority.

The Pap test is currently provided to tens of millions of women in tens of millions medical offices every year, usually during a routine gynecological examination. The procedure is non-invasive, painless, and fast. It involves inserting a brush (an endocervical brush) into the cervix and rotating the brush inside the cervix to collect cervical cells by gently scraping the cervical canal. Then the brush with the collected material is rinsed in a vial to release the cervical cells and discarded. The collected cells released into the rinsing liquid are analyzed for abnormalities indicative of cervical cancer and the DNA is analyzed for the presence of HPV, the causative agent of cervical cancer.

As the cervical canal is usually filled with cervical mucus, the material collected on the brush contains some visible amount of this mucus. This mucus within each sample normally has varying viscosity and solubility—from almost liquid consistency to almost gelatinous. After the brush with the sample is rinsed, the cervical mucus partly ends up released into the rinsing liquid and partly remains on the brush and ends up discarded with it.

SUMMARY

As described above, the cervical mucus remaining on the brush after rinsing is discarded in the course of the Pap test. Also, during the rinsing, some cervical mucus falls off or detaches from the brush without dissolving in the rinsing liquid; such undissolved cervical mucus also remains unused during Pap tests.

This undissolved cervical mucus on the brush and/or at the bottom of the rinsing vial, hereinafter called "rinsed cervical mucus" or just "rinsed mucus", is the focus of the following example embodiments.

Efficient harvesting of cells, cell fragments, free nuclei, and DNA material ("DNA material", as used in this application, includes, without limitation, DNA, DNA fragments, genomic DNA, and/or cell-free DNA) from female reproductive system is made possible by processing the rinsed cervical mucus (usually, gelatinous part of cervical mucus samples).

These cells, cell fragments, free nuclei, and/or DNA material may originate, for example, from ovarian, fallopian tubal, and endometrial tumors, benign or cancerous.

This DNA material accumulated in the rinsed cervical mucus can be harvested from the rinsed cervical mucus for a variety of medical or biological purposes.

If someone would choose to run a genomic analysis on the DNA material obtained from Pap test rinsing liquid, any information about ovarian, fallopian tubal, and endometrial tumors, if present, would be drowned by the overwhelming amount of genetic information from cervical cells.

On the other hand, the number of cervical cells present in the rinsed cervical mucus used in the example embodiments is significantly lower in comparison, making the DNA material harvested according to the disclosed methods much more valuable for genetic, genomic and epigenetic analysis.

This DNA material accumulated in the rinsed cervical mucus may be released from the mucus into a solution by a variety of methods including, without limitation, mechanical vibrations and other types of mechanical impact, by treating the mucus with emulsifier, or other chemical treatment to dissolve or reswell the rinsed cervical mucus.

The embodiments include a method comprising rinsing a cervical mucus sample comprising cervical cells in a rinsing liquid to release the cervical cells into the rinsing liquid and to produce a rinsed mucus sample; separating the rinsed mucus sample from the rinsing liquid and the cervical cells released into the rinsing liquid; and releasing of cells, cell fragments, free nuclei, and/or DNA material from the rinsed mucus sample.

Some embodiments further comprise lysing the cells, cell nuclei, or cell fragments released from the rinsed mucus sample.

In some embodiments, the releasing of cells, cell fragments, free nuclei, and/or DNA material from the rinsed mucus sample and the lysing of the released cells, cell nuclei, or cell fragments released from the rinsed mucus sample are performed simultaneously.

In some embodiments, the number of cervical epithelial cells rinsed off the cervical mucus sample during the rinsing of the cervical mucus sample in the rinsing liquid is greater than the number of cervical epithelial cells released from the rinsed mucus sample during the releasing of cells, cell fragments, free nuclei, and/or DNA material from the rinsed mucus sample.

In some embodiments, the separating of the rinsed mucus sample from the rinsing liquid and the cervical cells released into the rinsing liquid comprises aspiration, filtration, or centrifugation.

In some embodiments, the rinsed mucus sample is located on a mucus collector after the rinsing of the cervical mucus sample in the rinsing liquid to produce the rinsed mucus sample.

In some embodiments, the separating of the rinsed mucus sample from the rinsing liquid and the cervical cells released into the rinsing liquid comprises removing the mucus collector from the rinsing liquid.

In some embodiments, the cervical mucus sample is located on the mucus collector before the rinsing of the cervical mucus sample in the rinsing liquid to release the cervical cells into the rinsing liquid and to produce the rinsed mucus sample.

In some embodiments, the releasing of cells, cell fragments, free nuclei, and/or DNA material from the rinsed mucus sample comprises a chemical or mechanical treatment of the mucus sample or a combination thereof or treating the rinsed mucus sample with a compound comprising an emulsifier.

In some embodiments, the releasing of cells, cell fragments, free nuclei, and/or DNA material from the rinsed mucus sample comprises at least partially dissolving or reswelling the rinsed mucus sample in an emulsifier solution.

Some embodiments further comprise removing cells from the emulsifier solution and isolating DNA material from the emulsifier solution.

In some embodiments, the removing of cells from the emulsifier solution comprises filtration or centrifugation.

Some embodiments further comprise removing mucus from the emulsifier solution before isolating DNA material from the emulsifier solution.

The embodiments also include a method comprising rinsing a cervical mucus sample comprising cervical cells in a rinsing liquid to release the cervical cells into the rinsing liquid and to produce a rinsed mucus sample; separating the rinsed mucus sample from the rinsing liquid and the cervical cells released into the rinsing liquid; and lysing of cells, cell nuclei or cell fragments contained in the rinsed mucus sample.

In some embodiments the lysing of cells, cell nuclei, or cell fragments contained in the rinsed mucus sample comprises lysing the rinsed mucus sample.

The embodiments further include a method comprising rinsing a cervical mucus sample comprising cervical cells in a rinsing liquid to release the cervical cells into the rinsing liquid; removing the cervical cells released into the rinsing liquid from the rinsing liquid; and isolating DNA material from the rinsing liquid.

In some embodiments, the removal of cervical cells released into the rinsing liquid from the rinsing liquid comprises filtration or centrifugation.

Some embodiments further comprise removing mucus from the rinsing liquid before isolating DNA material from the rinsing liquid.

Some embodiments further comprise at least partially dissolving or reswelling the cervical mucus sample before the removal of the cervical cells released into the rinsing liquid from the rinsing liquid.

In some embodiments, the at least partially dissolving or reswelling of the cervical mucus sample before the removal of the cervical cells released into the rinsing liquid from the rinsing liquid occurs in a solution comprising emulsifier.

The embodiments further include a method comprising lysing a cervical mucus sample and cells contained therein in a lysing liquid to lyse the cervical mucus sample to release DNA material from the cervical mucus sample into the lysing liquid; and isolating DNA material from the lysing liquid.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

All illustrations of the drawings are for the purpose of describing selected versions of the present invention and are not intended to limit the scope of the present invention.

DETAILED DESCRIPTION

The cervical mucus sample may be obtained from the endocervix in a variety of ways using a variety of mucus collectors, for example, by using an endocervical brush, cervical brush, cytobrush, transcervical swab, broom-type sampling device, or spatula, by aspiration, by cervical lavage, intrauterine lavage, or by cervical probe. Example types of transcervical swabs are cotton, albumin coated, calcium alginate, rayon, Dacron, polyester, and polyurethane swab.

Figure 1:
FIG. 1 illustrates an example endocervical brush.
Figure 2:
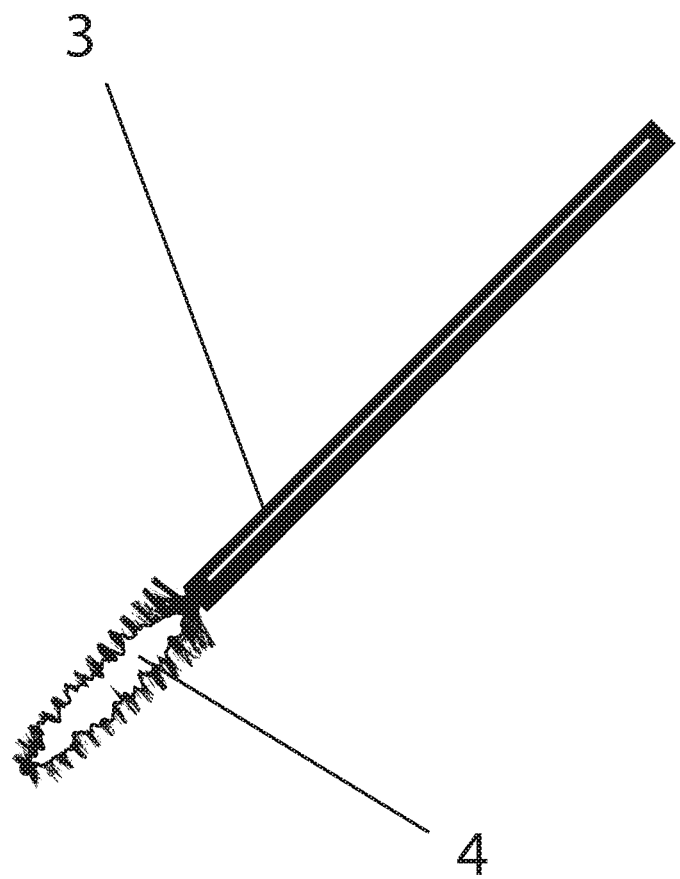
FIG. 2 illustrates an example endocervical brush with a cervical mucus sample.
Figure 3:
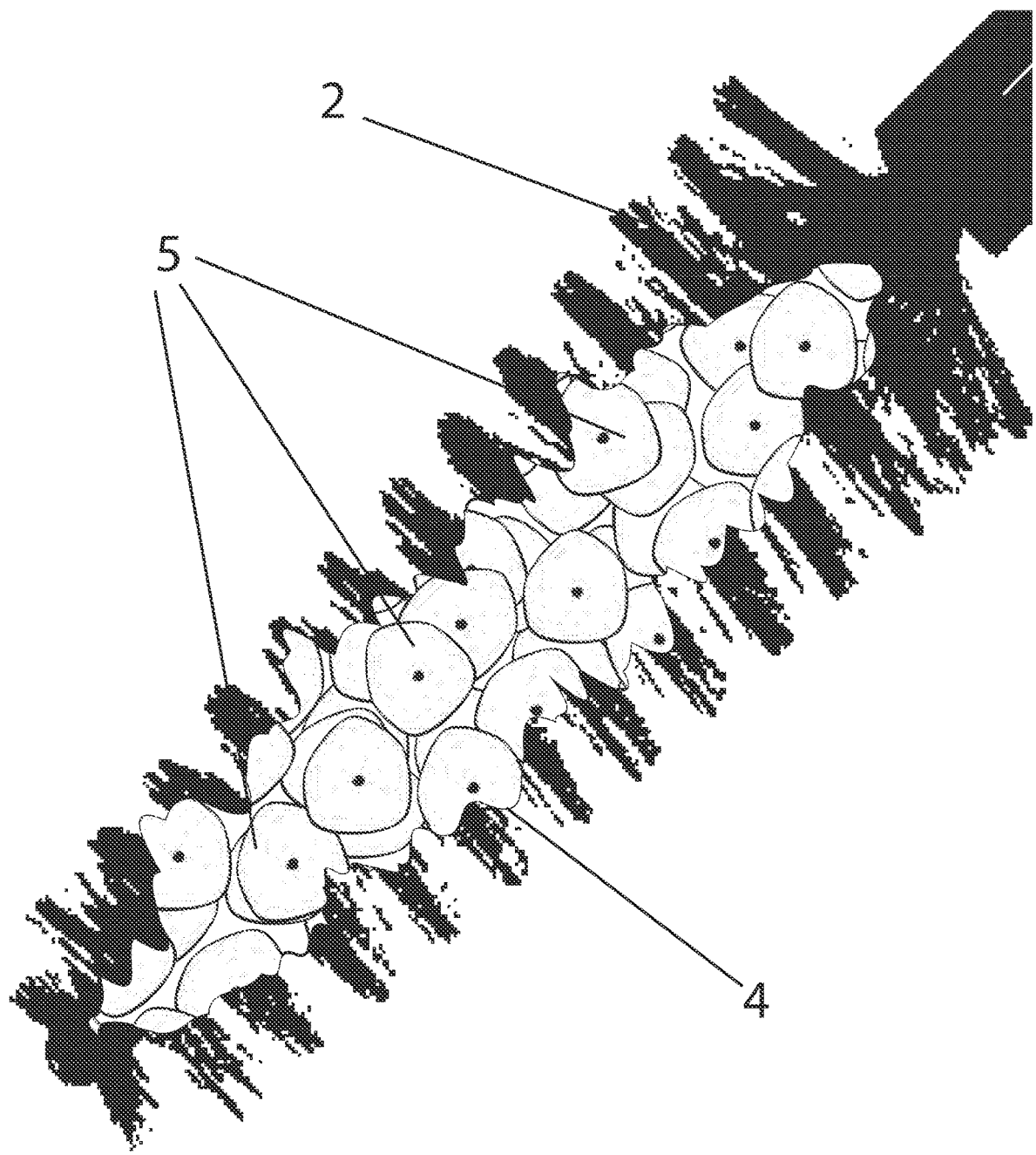
FIG. 3 illustrates an example endocervical brush with a cervical mucus sample and cervical cells within the sample.

The endocervical brush 3 shown in FIGS. 1-3 includes a handle 1 and brush bristles 2, which are inserted into a cervix to collect a cervical mucus sample 4 including a large number of cervical epithelial cells 5.

Figure 4:
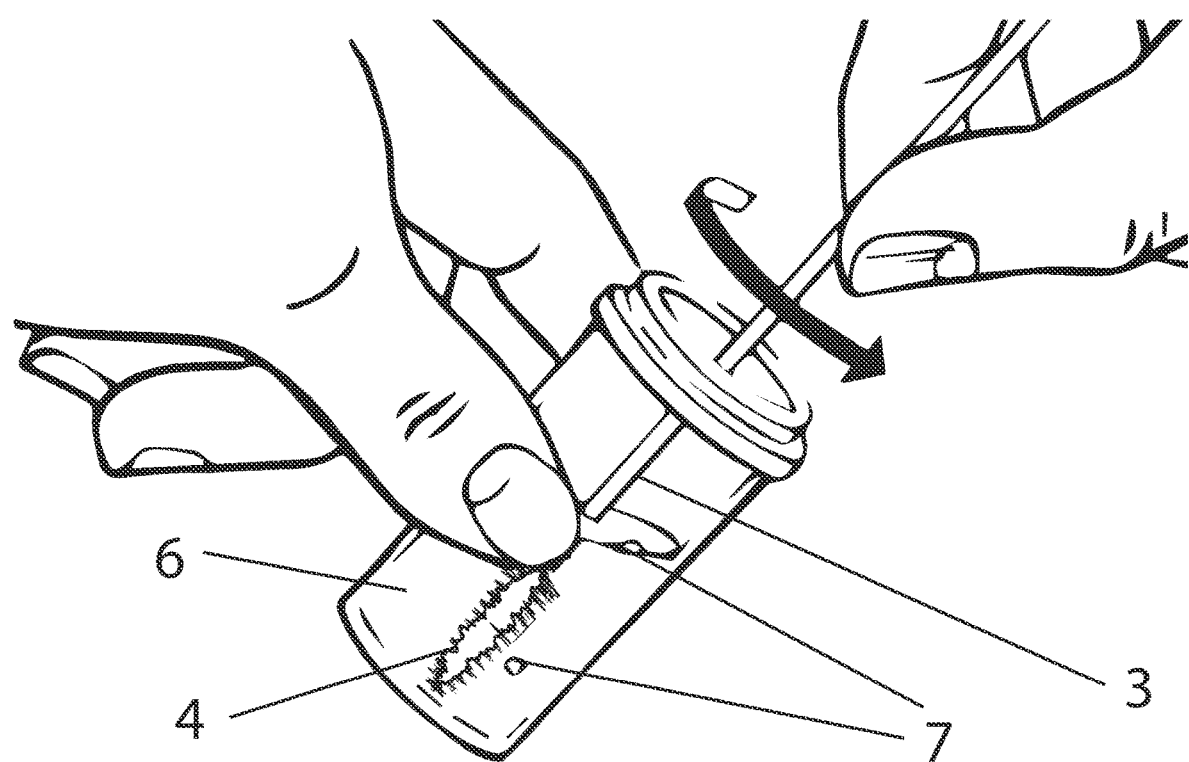
FIG. 4 illustrates rinsing of an example endocervical brush with a cervical mucus sample.

FIG. 4 shows rinsing of the cervical mucus sample 4 on the brush 3 in the rinsing liquid 6.

Some pieces 7 of the cervical mucus sample 4 may separate from the cervical mucus sample 4 during the rinsing and enter the rinsing liquid.

The rinsing may also remove some cellular and DNA material from the cervical mucus sample into the rinsing liquid 6.

The rinsing liquid 6 may be any liquid (including solutions) that preferably preserves the integrity of DNA and/or cell membranes, for example, without limitation, DNAgard Blood Tube formation, Streck Cell-Free DNA BCT formulation, saline solution, phosphate-buffered saline (PBS), or ThinPrep PreservCyt Solution. Alternative suitable liquids include, without limitation, ethyl alcohol, methanol, acetic acid, and sodium acetate.

During the rinsing, the sample 4 may be subjected to mechanical forces produced, for example, by vibration, shaking, and/or swirling.

Figure 5:
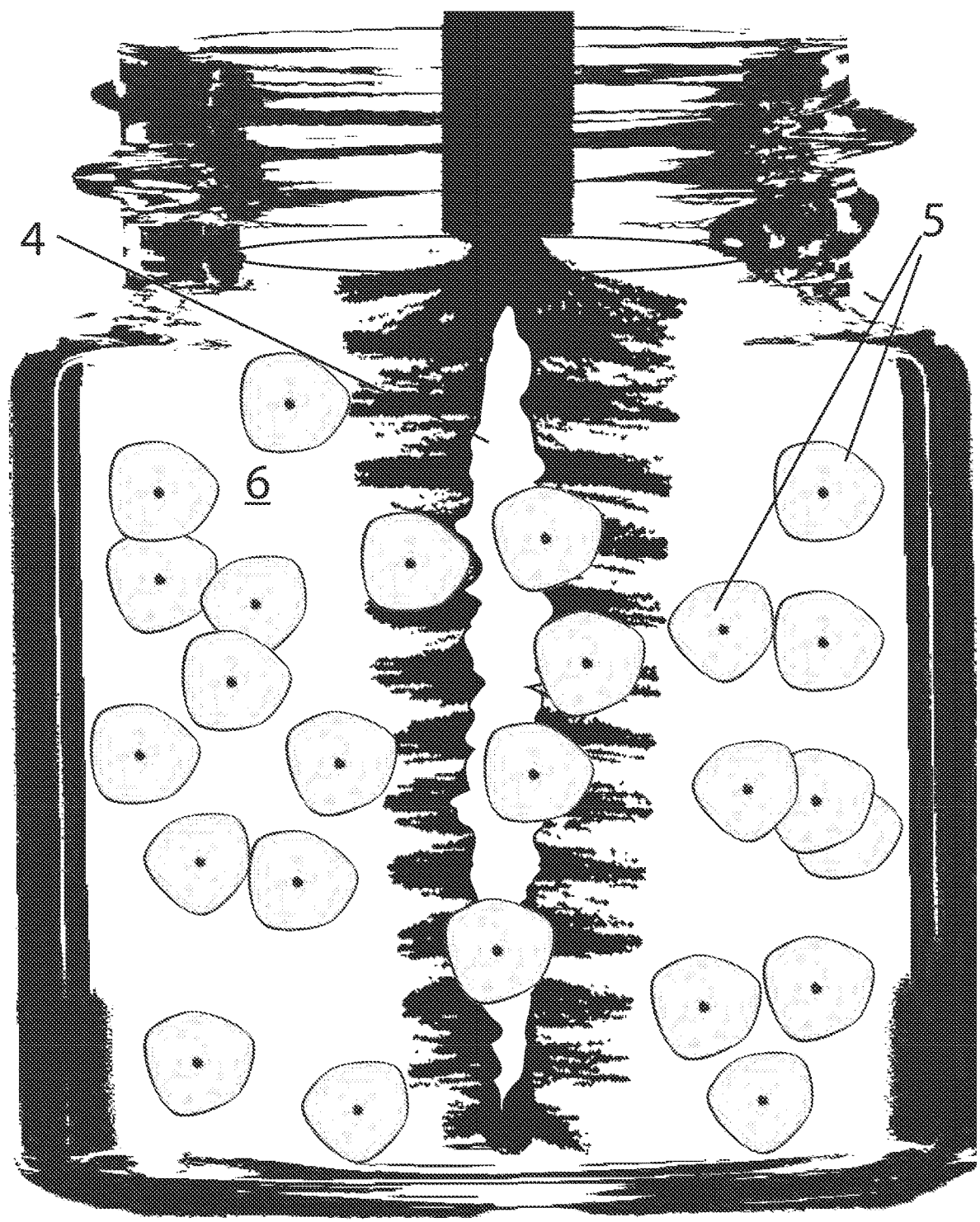
FIG. 5 illustrates rinsing of an example endocervical brush with a cervical mucus sample and cervical cells in the rinsing liquid.

FIG. 5 shows a large number of cervical epithelial cells 5 released and entering the rinsing liquid 6 from the cervical mucus sample 4 during its rinsing.

Figure 6:
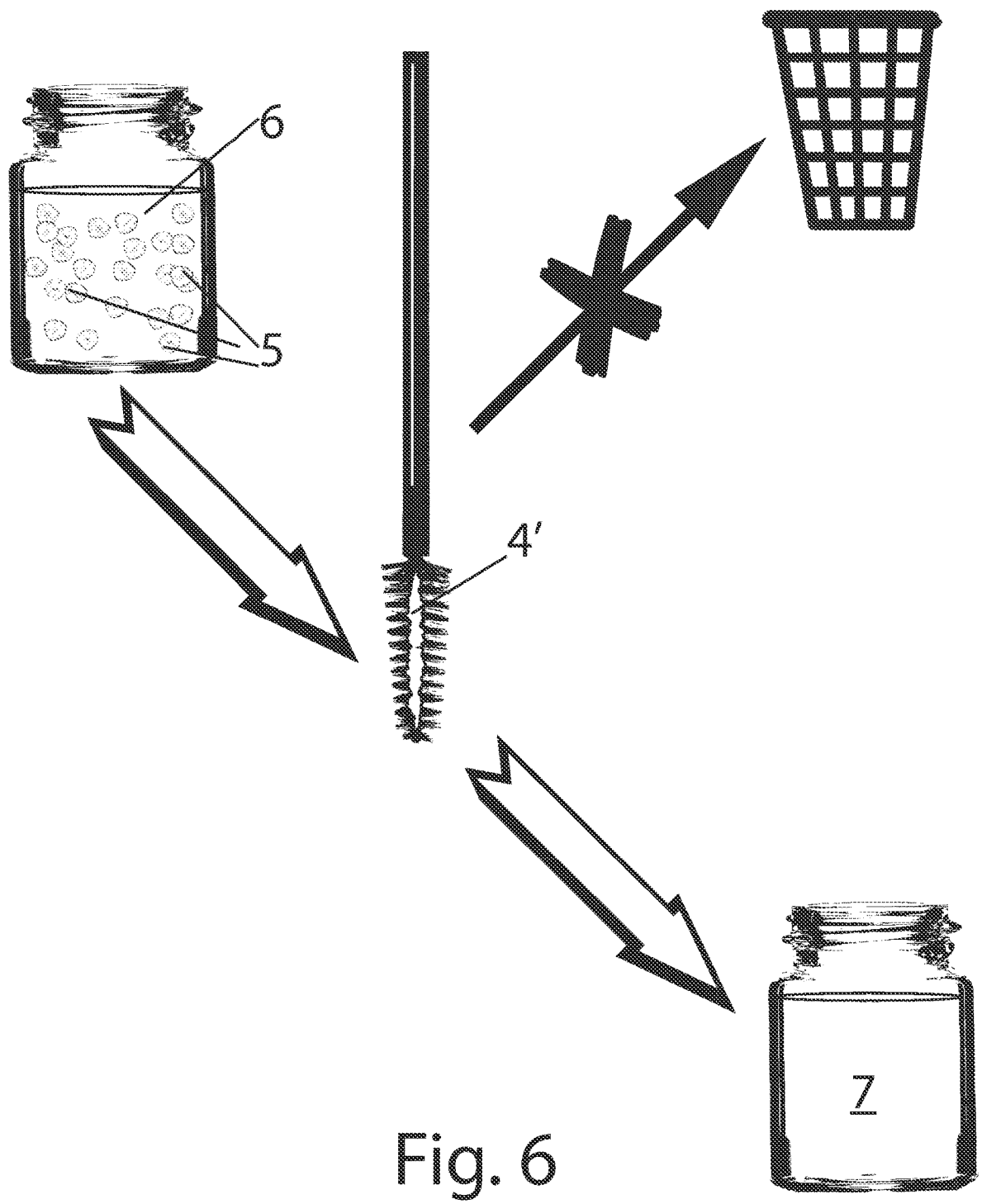
FIG. 6 illustrates transferring of an example endocervical brush with a rinsed mucus sample from the rinsing liquid into a chemical treatment liquid.

FIG. 6 shows a rinsed mucus sample 4' (which is normally discarded in the course of a Pap test) being separated and removed from the rinsing liquid 6 (and the cervical cells 5 in the rinsing liquid 6) and transferred instead (on a mucus collector, such as a brush) to a liquid 7 for chemical preservation and/or chemical and/or mechanical treatment; for example, for treating the rinsed mucus sample 4' with an emulsifier.

The rinsed mucus sample may additionally or alternatively include one or several fragments of rinsed cervical mucus (usually, relatively more gelatinous mucus) floating or on the bottom of the vessel where the rinsing took place. In such cases the mucus collector used for mucus separation may be, for example, a sieve, a hook, or any device capable of catching chunks of mucus in a liquid.

The rinsed mucus sample may also be separated from the rinsing liquid 6 (and the cervical cells 5 in the rinsing liquid 6) by aspiration, filtration, or centrifugation for subsequent transfer to the liquid 7.

The rinsed mucus sample comprises (possibly at least partially collapsed or dehydrated) relatively gelatinous mucus (poorly soluble or not soluble in water or saline) with a variety of biologic material embedded therein including cells, cell fragments, free nuclei, and DNA material from female reproductive system. Therefore, the rinsed mucus sample contains the embedded biological material not available for diagnostic methods analyzing the biological material rinsed off cervical samples.

Figure 7:
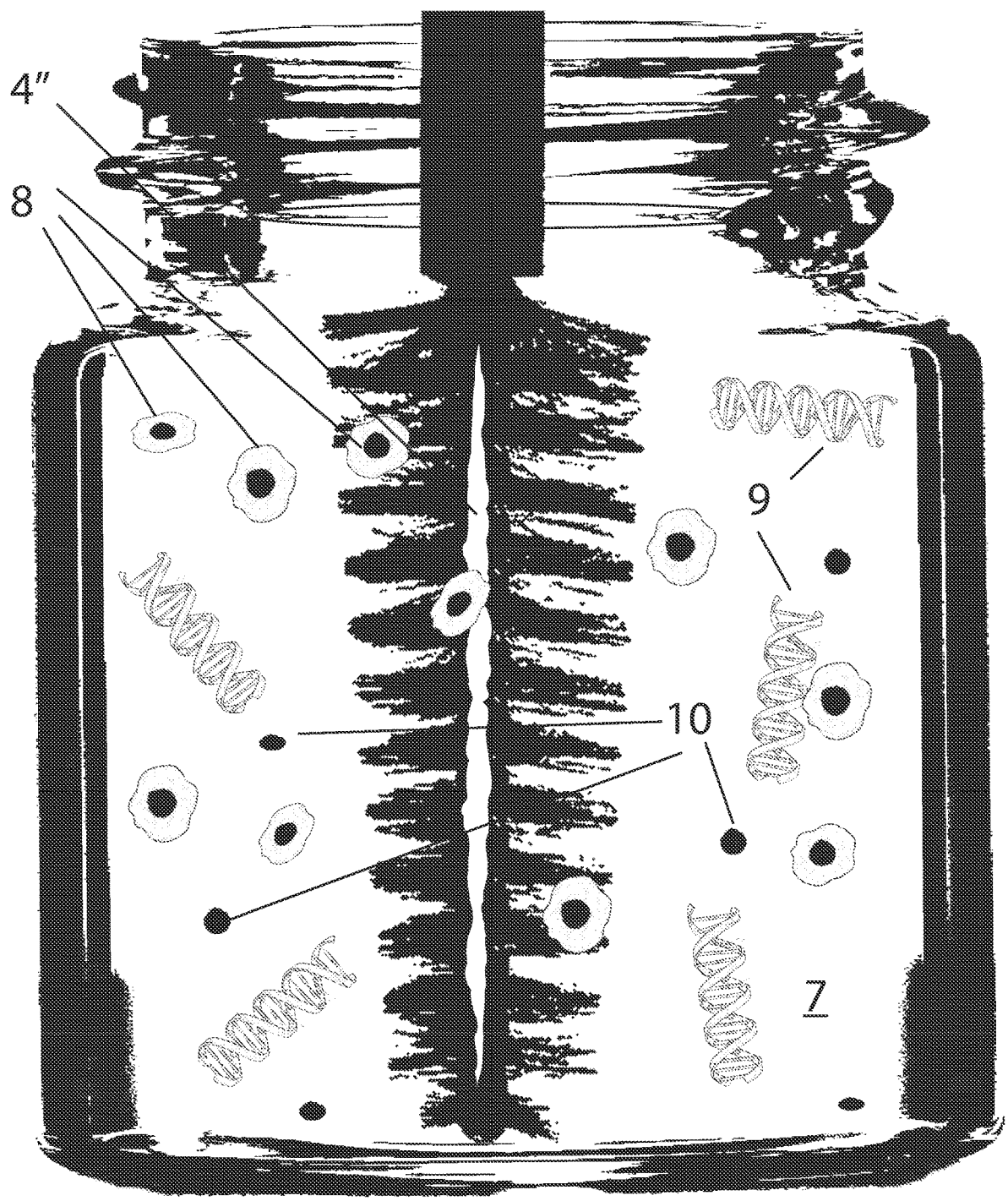
FIG. 7 illustrates treating an example endocervical brush with a rinsed mucus sample to release non-cervical cells, cell fragments, free nuclei, and/or DNA material.

FIG. 7 shows the rinsed cervical mucus 4' (now labeled 4") after being at least partially dissolved, disintegrated, and/or swollen in the liquid 7, for example, by using an emulsifier, such as Polysorbate 20, Tergitol-type NP-40, polyethylene glycol, or triethanolamine. Alternative emulsifiers include ethanolamine, hydroxypropyl methyl cellulose, and propylene glycol.

Alternatively, or additionally, the rinsed cervical mucus 4' may have been subjected to mechanical forces produced, for example, by vibration, shaking, and/or swirling. The cells 8 (including tumor cells) and/or cell fragments and free nuclei 10 and/or DNA material 9 that used to be contained in the rinsed cervical mucus 4' are now released into the liquid 7.

The number of cervical epithelial cells rinsed off the cervical mucus sample into the rinsing liquid 5 is greater than the number of cervical epithelial cells remaining in rinsed mucus sample after rinsing and then released from the rinsed mucus sample during the treatment in the liquid 7. In other words, the rinsing beneficially removes the majority of cervical epithelial cells from the subsequent processing and analysis.

The released cells, cell fragments, free nuclei, and/or DNA material in the liquid 7 may now be extracted from the liquid 7 for subsequent use.

In particular, the released cells 8 may be isolated or removed from the liquid 7, for example, by filtration (wherein the filter, for example, comprises pores from about 40 microns to about 120 microns) or centrifugation. Such filtration or centrifugation would also remove any pieces of mucus remaining in the liquid 7.

These cells 8 may be used for cytological analysis, for example, Papanicolaou staining or antibody staining, or for cellular imaging, for example, using technologies offered by VisionGate, Inc.

The released cells 8 may also be collected and lysed to release the genomic DNA using a denaturing solution, for example, sodium dodecyl sulfate (SDS) with the concentration or up to 0.5%, or a solution with a high concentration of chaotropic salts, for example, 6 M guanidine-HCL or 6-8 M urea. The lysing liquid may also include, for example, Proteinase K, with the typical working concentration 50-100 µg/ml.

Figure 8:
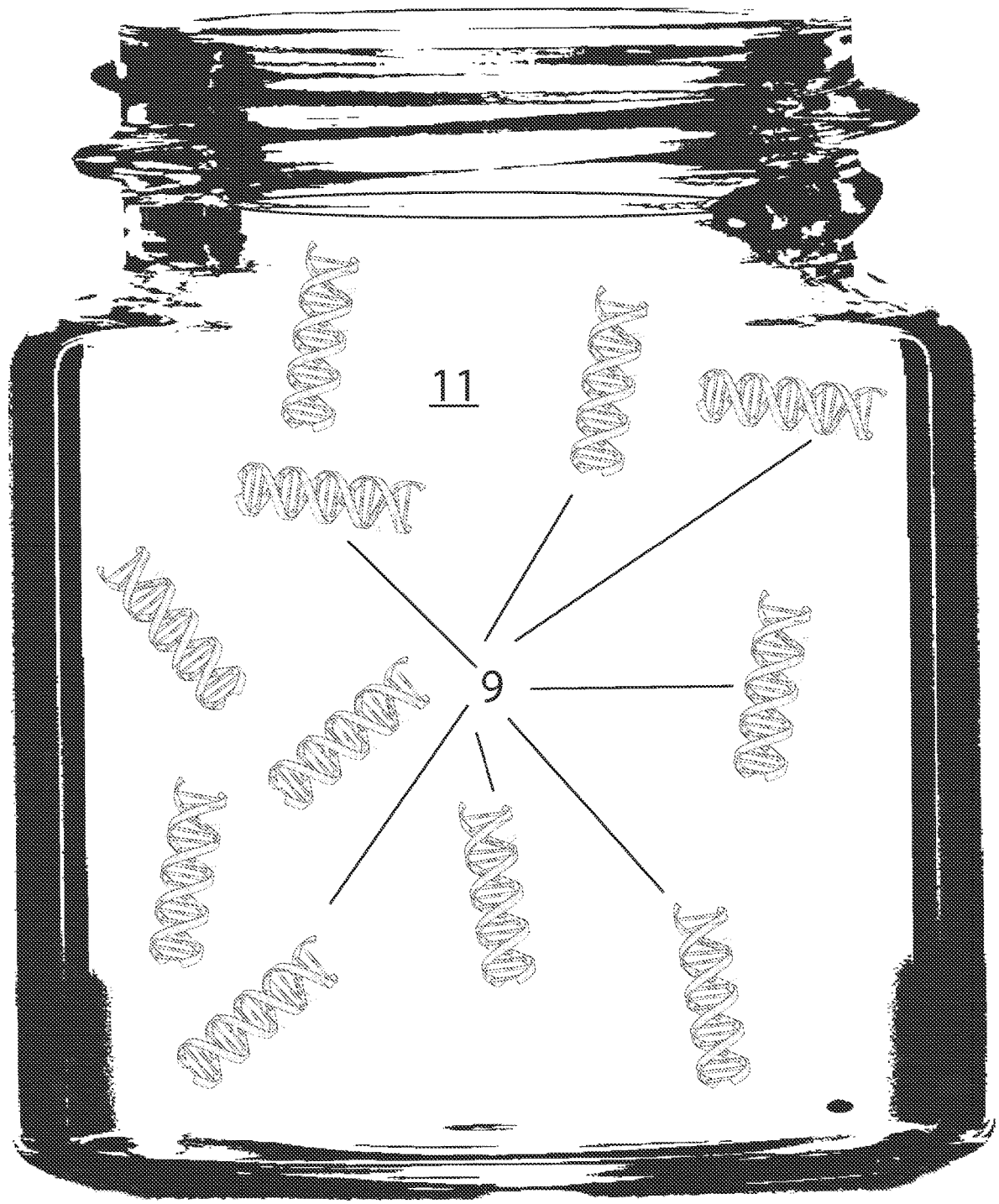
FIG. 8 shows DNA material in the lysing solution after the released non-cervical cells, free nuclei, and cell fragments are lysed.

FIG. 8 shows the DNA material 9 that had been released into the liquid 7 and those that were simultaneously or subsequently released from the cells 8 (including tumor cells) and cell fragments or free nuclei 10 after lysing in the lysing liquid 11.

The rinsed cervical mucus 4' may also be lysed using a lysing liquid 11 without prior treatment in the liquid 7 so that the cervical mucus (formed by a latticework of mucin molecules) in the rinsed cervical sample 4' at least partly disintegrates, as well as the cells, cell fragments, and free nuclei contained in the rinsed cervical sample 4'. Such lysing also releases DNA material 9 from the rinsed cervical sample and from cells, cell fragments, and free nuclei contained therein into the lysing liquid 11.

The lysing liquid 11 may include, for example, Proteinase K, with the typical working concentration 50-100 µg/ml. The lysing liquid 11 may also include a denaturing agent, for example, sodium dodecyl sulfate (SDS), with the concentration of up to 0.5%, or contain a high concentration of chaotropic salts, for example, 6 M guanidine-HCL or 6-8 M urea.

Another way of obtaining DNA material 9 from the cervical mucus sample 4 is to remove substantially all cells from the rinsing liquid 6, after the rinsing shown in FIG. 4.

In particular, the cells may be removed from the rinsing liquid 6, for example, by filtration (wherein the filter, for example, comprises pores from about 40 microns to about 120 microns) or centrifugation. Such filtration or centrifugation would also remove any pieces of mucus remaining in the rinsing liquid 6.

Before the removal of cells from the rinsing liquid 6 the cervical mucus sample 4 may be at least partially dissolved, disintegrated, and/or swollen, for example, by using an emulsifier, such as Polysorbate 20, Tergitol-type NP-40, polyethylene glycol, or triethanolamine. Alternative emulsifiers include ethanolamine, hydroxypropyl methyl cellulose, and propylene glycol.

Alternatively, or additionally, the cervical mucus sample 4 may be subjected to mechanical forces produced, for example, by vibration, shaking, or swirling.

Alternatively, cervical mucus sample 4 on the brush 3, instead of the rinsing liquid 6, may be submerged straight into a lysing liquid 7 capable of at least partially lysing the cervical mucus sample 4 and the cells 8 (including tumor cells) and/or cell fragments and/or free nuclei 10 within the sample 4 (for example, using one of the lysing liquids recited hereinabove) to release DNA material from the cervical mucus sample 4 and its content into the lysing liquid.

The DNA material 9 released into and remaining in the rinsing liquid 6, the liquid 7, or the lysing liquid 11 may be isolated, for example, by using any cell-free DNA-isolation method or commercially available kit, for example, QIAamp Circulating Nucleic Acid Kit from QIAGEN or magnetic bead technology, for example, from Thermo Fisher Scientific, Inc.

The isolated DNA fragments, genomic DNA, cell-free DNA fragments, or cell-free DNA may be tested for one or more mutations selected from the group consisting, for example, of CTNNB1, EGFR, PI3KCA, PTEN, TP53, BRAF, KRAS, AKT1, NRAS, PPP2R1A, APC, FBXW7, ARID1A, CDKN2A, MLL2, RNF43, and/or FGFR2. The mutations may be selected from the group consisting of a missense mutation, a nonsense mutation, and an indel. Detection of such mutations indicates likelihood of the presence of such a cancer in the patient.

The isolated DNA material may also be tested for epigenetic modifications.

A kit for use in the disclosed methods may include a carrier for the various components. The carrier can be a container or support, in the form of, e.g., bag, box, tube, rack, and is optionally compartmentalized. The kit also includes various components useful in obtaining, rinsing, processing, storing, and transporting the mucus sample using the above-discussed techniques. For example, the detection kit may include one or more solutions, such as DNAgard Blood Tube formation, Streck Cell-Free DNA BCT formulation, saline solution, phosphate-buffered saline (PBS), or ThinPrep PreservCyt Solution. The kit may also include a device for collecting mucus, for example, an endocervical brush, an aspiration device, or a cervical probe.

Although the invention has been explained in relation to its preferred embodiment, it is to be understood that many other possible modifications and variations can be made without departing from the spirit and scope of the invention as hereinafter claimed. While this invention has been particularly shown and described with references to preferred embodiments thereof, it will be understood by those skilled in the art that various changes in form and details may be made therein without departing from the scope of the invention encompassed by the appended claims.

The invention claimed is:

1. A method for detecting genetic or epigenetic changes associated with ovarian, fallopian tubal or endometrial cancer in a cervical mucus sample isolated from a subject, comprising:
   (a) rinsing a mucus collector holding the cervical mucus sample comprising cervical and non-cervical cells, wherein the rinsing is performed in a rinsing liquid to rinse off the cervical cells from the cervical mucus sample held on the mucus collector into the rinsing liquid and to produce a rinsed mucus sample held on the mucus collector comprising non-cervical cells;
   (b) after the step (a), separating the mucus collector holding the rinsed mucus sample comprising non-cervical cells from the rinsing liquid and from the cervical cells rinsed off into the rinsing liquid in the step (a);
   (c) after the step (b), releasing cells, cell fragments, free nuclei, and/or DNA material from the rinsed mucus sample remaining held on the mucus collector after the step (b) comprising non-cervical cells, cell fragments, free nuclei, and/or DNA material, wherein the releasing comprises exposing the rinsed mucus sample remaining held on the mucus collector after the step (b) to a solution comprising an emulsifier;
   (d) lysing cells, cell fragments and/or free nuclei released from the rinsed mucus sample comprising non-cervical cells to release DNA; and
   (e) analyzing the DNA released in steps (c) and (d) for the presence of a genetic and/or epigenetic change in one or more genes associated with ovarian, fallopian tubal or endometrial cancer, wherein the presence of said genetic and/or epigenetic change is indicative of the presence of said cancer in the subject.

2. The method of claim 1, wherein the step (c) and the step (d) are performed simultaneously.

3. The method of claim 1, wherein the number of cervical epithelial cells rinsed off the mucus sample during the step (a) is greater than the number of cervical epithelial cells released during the step (c).

4. The method of claim 1, wherein the method is for detecting genetic or epigenetic changes associated with ovarian or fallopian tubal cancer and step (e) comprises analyzing the DNA released in steps (c) and (d) for a genetic and/or epigenetic change in one or more genes associated with ovarian or fallopian tubal cancer.

5. A method for detecting genetic or epigenetic changes associated with ovarian, fallopian tubal or endometrial cancer in a cervical mucus sample isolated from a subject, comprising:
   (a) rinsing a mucus collector holding the cervical mucus sample comprising cervical and non-cervical cells, wherein the rinsing is performed in a rinsing liquid to rinse off the cervical cells from the cervical mucus sample held on the mucus collector into the rinsing liquid and to produce a rinsed mucus sample held on the mucus collector comprising non-cervical cells;
   (b) after the step (a), separating the mucus collector holding the rinsed mucus sample comprising non-cervical cells from the rinsing liquid and from the cervical cells rinsed off into the rinsing liquid in the step (a);
   (c) after the step (b), lysing cells, cell fragments and/or free nuclei contained in the rinsed mucus sample comprising non-cervical cells remaining held on the mucus collector after the step (b) to release DNA; and
   (d) analyzing the DNA released in step (c) for the presence of a genetic and/or epigenetic change in one or more genes associated with ovarian, fallopian tubal or endometrial cancer, wherein the presence of said genetic and/or epigenetic change is indicative of the presence of said cancer in the subject.

6. The method of claim 5, wherein the method is for detecting genetic or epigenetic changes associated with ovarian or fallopian tubal cancer and step (d) comprises analyzing the DNA released in steps (c) and (d) for a genetic and/or epigenetic change in one or more genes associated with ovarian or fallopian tubal cancer.

* * * * *

UNITED STATES PATENT AND TRADEMARK OFFICE
CERTIFICATE OF CORRECTION

| | |
|---|---|
| PATENT NO. | : 11,230,729 B2 |
| APPLICATION NO. | : 16/278151 |
| DATED | : January 25, 2022 |
| INVENTOR(S) | : Maya Tevlin |

It is certified that error appears in the above-identified patent and that said Letters Patent is hereby corrected as shown below:

On the Title Page

Item (73), please replace "Inanna Diagnostics, Inc, Bayside, NY (US)" as the Assignee with the following Assignee: "Inanna Diagnostics, Inc., Bayside, NY (US)"

Signed and Sealed this
Fourteenth Day of February, 2023

*Katherine Kelly Vidal*

Katherine Kelly Vidal
*Director of the United States Patent and Trademark Office*